(12) United States Patent  
Ueberle

(10) Patent No.: US 6,640,139 B1  
(45) Date of Patent: Oct. 28, 2003

(54) THERMAL THERAPY WITH TISSUE PROTECTION

(75) Inventor: Friedrich Ueberle, Gilching (DE)

(73) Assignee: Dornier MedTech Holding International GmbH, Bavaria (DE)

( * ) Notice: Subject to any disclaimer, the term of this patent is extended or adjusted under 35 U.S.C. 154(b) by 0 days.

(21) Appl. No.: 09/786,805

(22) PCT Filed: Oct. 20, 1998

(86) PCT No.: PCT/EP98/06687

§ 371 (c)(1),  
(2), (4) Date: Mar. 7, 2001

(87) PCT Pub. No.: WO00/23147

PCT Pub. Date: Apr. 27, 2000

(51) Int. Cl.[7] ................................................. A61F 2/00
(52) U.S. Cl. ....................................... 607/102; 607/101
(58) Field of Search ....................... 607/98–99, 101–105

(56) References Cited

U.S. PATENT DOCUMENTS

| | | | |
|---|---|---|---|
| 5,320,617 A | | 6/1994 | Leach .......................... 606/15 |
| 5,321,715 A | | 6/1994 | Trost ........................... 372/69 |
| 5,437,673 A | | 8/1995 | Baust et al. .................... 606/23 |
| 5,509,929 A | | 4/1996 | Hascoet et al. ............. 607/101 |
| 5,861,021 A | * | 1/1999 | Thome et al. ............... 607/101 |
| 5,906,636 A | * | 5/1999 | Casscells et al. ............. 607/96 |
| 6,006,755 A | * | 12/1999 | Edwards ...................... 128/898 |
| 6,071,956 A | * | 6/2000 | Slepian et al. .............. 514/496 |
| 6,190,355 B1 | * | 2/2001 | Hastings .................. 604/96.01 |
| 6,216,041 B1 | * | 4/2001 | Tierney et al. .............. 607/101 |
| 6,273,886 B1 | * | 8/2001 | Edwards et al. .............. 606/34 |
| 6,451,044 B1 | * | 9/2002 | Naghavi et al. .............. 607/96 |

FOREIGN PATENT DOCUMENTS

EP         0 428 875 B1     10/1994    ............. A61F/7/12

* cited by examiner

*Primary Examiner*—Roy D. Gibson  
(74) *Attorney, Agent, or Firm*—Holmes J. Hawkins, III; King & Spalding, LLP.

(57) ABSTRACT

A thermotherapy device for treatment of diseased biological tissues includes an outer lumen and at least one inner lumen. Preheating of non-target tissue is carried out during a desensitizing mode of the thermotherapy process at a temperature that is sublethal to cells of the non-target tissue structure but is high enough to provoke the building of heat shock proteins for protecting non-target tissue structures during the thermotherapy process. Then during a destructive mode of the thermotherapy process, an energy source is insertable into one of the lumens in carry out a heating protocol to treat the enlarged tissue while the non-target tissue is protected by shock proteins produced during the desensitizing mode of the process. The energy source can be microwave, ultrasound or other energy source, and a temperature sensing device can be used in controlling the energy source for effective treatment.

12 Claims, 13 Drawing Sheets

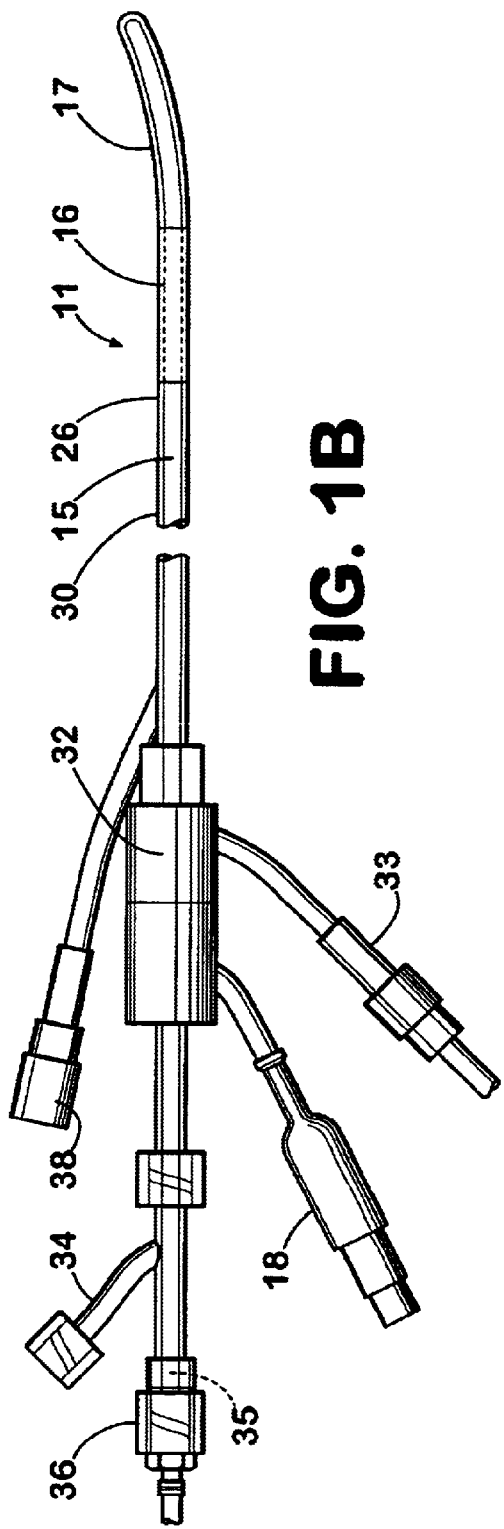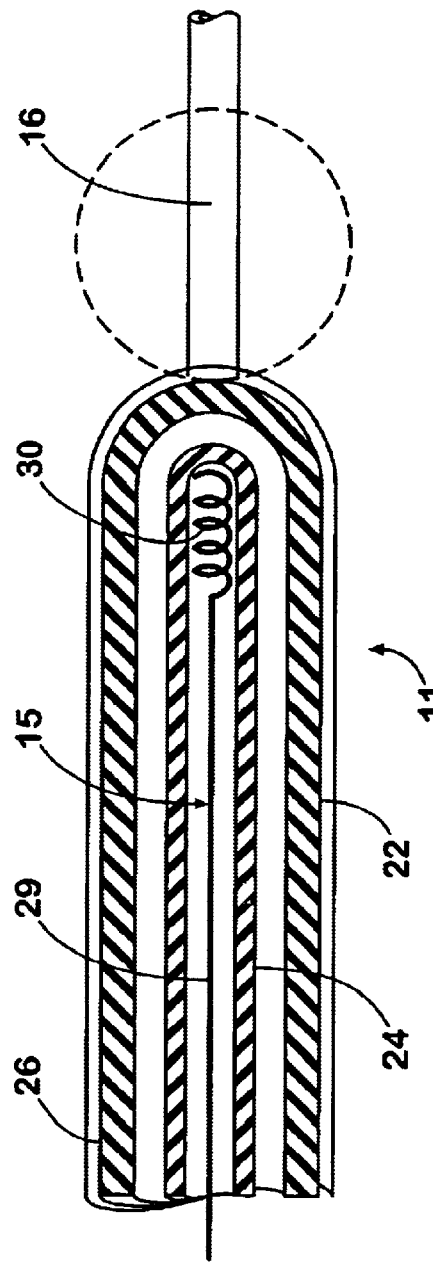
FIG. 1B
FIG. 2

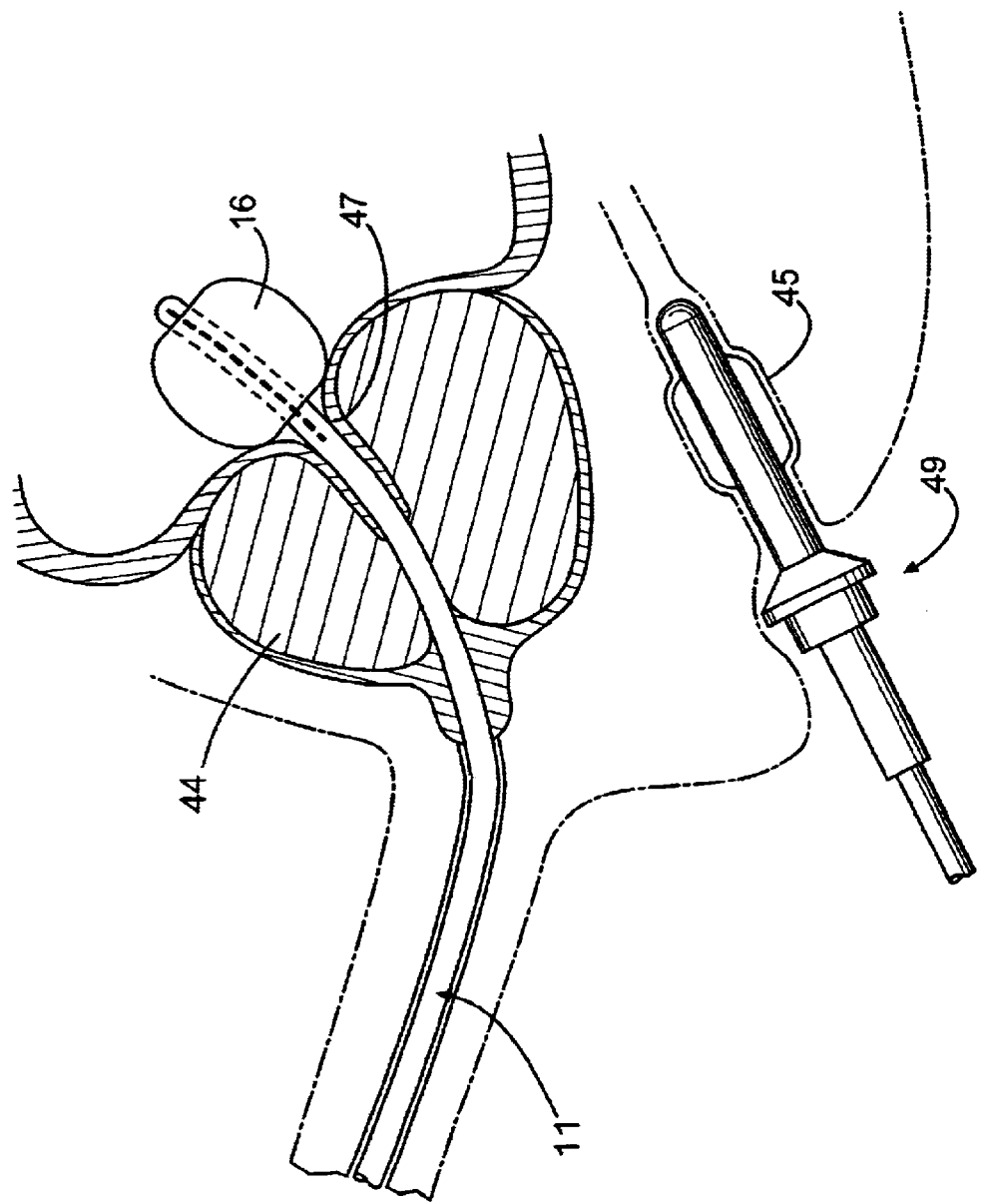

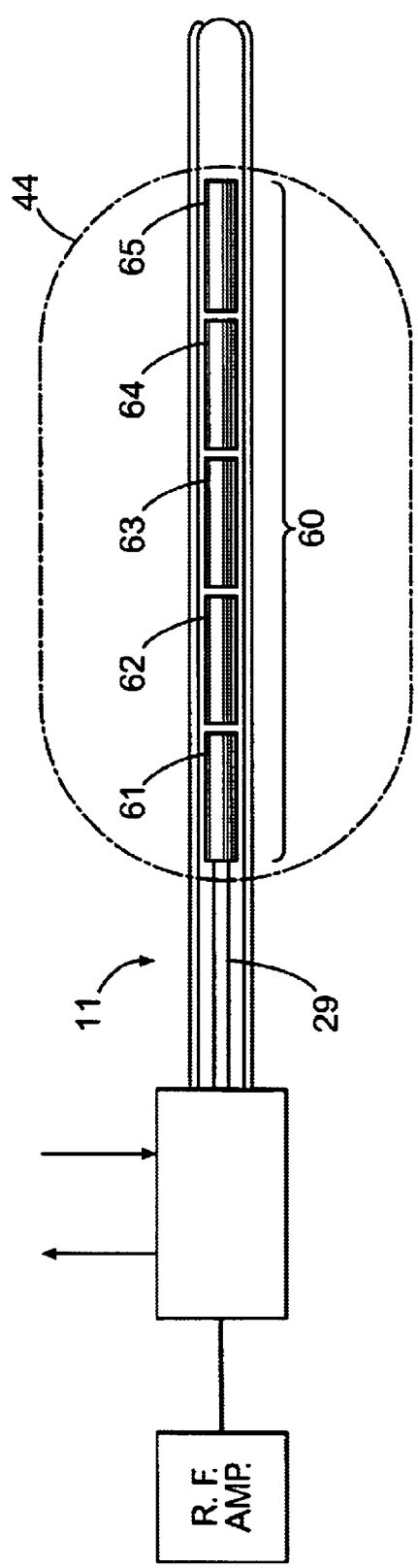
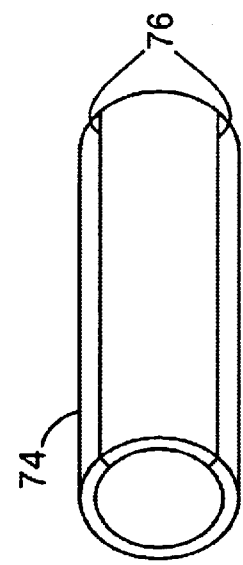
FIG. 11D
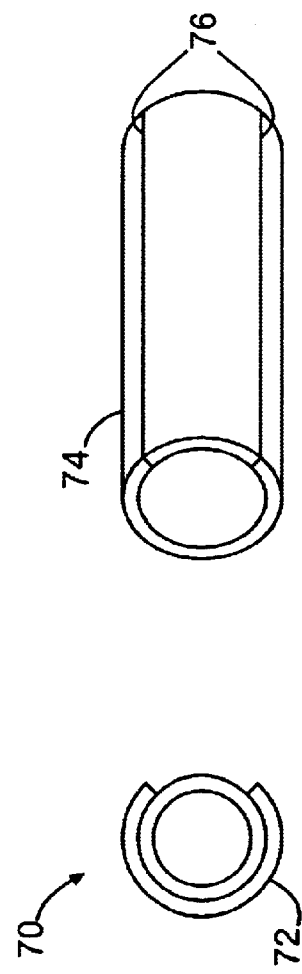
FIG. 11C
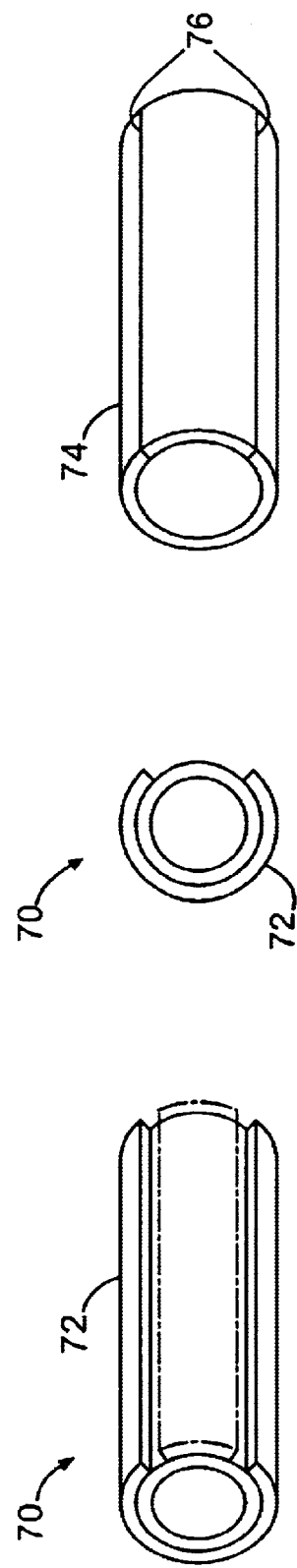
FIG. 11B
FIG. 11A

THERMAL THERAPY WITH TISSUE PROTECTION

BACKGROUND OF THE INVENTION

The present invention relates generally to an apparatus and method for performing a thermal therapy patient treatment protocol. More particularly, the invention relates to a novel apparatus and method for inducing non-target tissue to generate a heat protective response and then irradiating and/or heating target tissue, such as the prostate gland, for therapeutic purposes.

Thermotherapy treatment is a relatively new method of treating diseased and/or undesirably enlarged human tissues. Hyperthermia treatment is well known in the art, involving the maintaining of a temperature between about 41.5° C. through 45° C. Thermotherapy usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of larger amounts of energy to the target tissues. At the same time, it is important to protect non-target tissues from the high thermotherapy temperatures used in the treatment. Providing safe and effective thermotherapy, therefore, requires devices which have further capabilities compared to those which are suitable for hyperthermia.

Though devices and methods for treating benign prostatic hyperplasia have evolved dramatically in recent years, further progress is needed. As recently as 1983, medical textbooks recommended surgery for removing impinging prostatic tissues and four different surgical techniques were utilized. Suprapubic prostatectomy was a recommended method of removing the prostate tissue through an abdominal wound. Significant blood loss and the concomitant hazards of any major surgical procedure were possible with this approach.

Perineal prostatectomy was an alternatively recommended surgical procedure which involved gland removal through an incision in the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating benign prostatic hyperplasia. Researchers began to incorporate heat sources in Foley catheters after discovering that enlarged mammalian tissues responded favorably to increased temperatures. Examples of devices directed to treatment of prostate tissue include U.S. Pat. No. 4,662,383 (Harada), U.S. Pat. No. 4,967,765 (Turner), U.S. Pat. No. 4,662,383 (Sogawa) and German Patent No. DE 2407559 C3 (Dreyer). Though these references disclose structures which embody improvements over the surgical techniques, significant problems still remain unsolved.

Recent research has indicated that enlarged prostate glands are most effectively treated with higher temperatures than previously thought. Complete utilization of this discovery has been tempered by difficulties in shielding rectal wall tissues and other non-target tissues. While shielding has been addressed in some hyperthermia prior art devices, the higher microwave energy field intensities associated with thermotherapy necessitate structures and methods having further capabilities beyond those suitable for hyperthermia which protect non-target tissues effectively. For example, the symmetrical devices disclosed in the above-referenced patents have generally produced relatively uniform cylindrical energy fields. Even at the lower microwave energy field intensities encountered in hyperthermia treatment, unacceptably high rectal wall temperatures have severely limited treatment periods and effectiveness. Accordingly, various new shielding methods and apparatus have been proposed recently to attempt to prevent all thermal energy from reaching non-target tissues such as the rectal wall.

In addition, efficient and selective cooling of the devices is rarely provided. This can increase patient discomfort and increases the likelihood of non-target tissue damage.

It is well known that different types of cells are differently susceptible to heat. For example, tumor cells can be killed at thermal doses that are lower than those doses necessary to destroy adjacent normal tissue. This knowledge can be used for therapy planning purpose, but this often leads to problems because the thermal fields are not sufficiently predictable in the body, because natural cooling mechanisms by blood perfusion cannot be modeled exactly. Thus, to kill all malignant cells with higher confidence, it is necessary to enhance the thermal dose either by raising the temperature or applying the thermal energy several times using a sequenced therapy approach.

Both enhancement strategies are known to have problems. On the one hand, the application of higher temperatures increases the risk of destroying non-target tissue structures. For example, in the treatment of prostate tissue for reducing the effect of a benign prostate hyperplasia (BPH) or for destroying prostate cancer tumors, an overheating of the rectal wall can lead to severe complications such as the creation of a fistula, and the overheating of the sphincter muscles can lead to incontinence.

If, on the other hand. a sequenced treatment mode is chosen, it has been found that the tissue builds up a protection by "heat shock proteins", which decrease the effect of subsequent conventional therapies dramatically. From in vitro tests, it is known that tissue, protected by heat shock proteins, can survive temperatures up to 20° C. higher than non-protected tissue. These heat shock proteins have a life of 20 to 40 hours in vitro and possibly up to several days in vivo.

It is therefore an object of the invention to provide an improved apparatus and method suitable for thermotherapy or hyperthermia treatment.

It is a further object of the invention to provide an improved apparatus and method for thermotherapy treatment which provides substantially uniform irradiation of target tissues while effectively protecting non-target tissues from the temperatures of treatment.

It is another object of the invention to provide an improved thermotherapy device which includes a collimated irradiation of a target zone generally and selective cooling of non-target tissues.

It is still an additional object of the invention to provide an improved thermotherapy device which reduces tissue damage and discomfort by stimulating non-target tissues to generate heat shock proteins.

SUMMARY OF THE INVENTION

The present invention provides thermotherapy apparatus for protecting non-target tissue structures from unintended damage during thermotherapy treatment of target tissue located adjacent to the non-target tissue structures. Unlike prior art methods and apparatus which limit or prevent thermal energy from reaching non-target tissue, the present invention actually applies controlled thermal energy to non-target tissue. The thermotherapy apparatus comprises a thermotherapy probe preferably including an outer lumen, an inner lumen, and an energy source including an applicator portion that is adapted to be inserted into one of the lumens. A controller is operable in a first treatment mode for causing a heating medium to be supplied to one of the lumens for heating non-target tissue structures to be protected to a temperature that is sublethal to non-target tissue but is high enough to provoke the building of heat shock proteins in the non-target tissue. The controller is operable in a second treatment mode to control the energy source to provide heating of the target tissues to a second temperature that is high enough to kill a desired cell mass contained in the target tissue structure. The heat shock proteins substantially prevent destruction of the non-target tissue structures during the second treatment mode.

Further in accordance with the invention, there is provided a method for protecting non-target tissue structures of a patient's body from unintended damage during thermotherapy treatment of target tissue located adjacent to the non-target tissue structures. The method includes the steps of: inserting into the patient's body a thermotherapy probe including inner and outer lumens; pumping a heated liquid through the inserted thermotherapy probe for heating the non-target tissue structures in a first treatment mode to a first temperature that is sublethal to tissue structures but is high enough to provoke the building of heat shock proteins in the non-target tissue structures; positioning an applicator portion of an energy source in at least one of the lumens; and applying radiative energy from the energy source to the target tissue in a second treatment mode for heating the target tissue to a second temperature that is high enough to kill a desired cell mass contained in the target tissue.

Other advantages and features of the invention will become apparent from the following detailed description and claims and also in the drawings described herein below.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

FIG. 1B is a top plan view of thermotherapy probe of the thermotherapy apparatus of FIG. 1A;

FIG. 2 is an enlarged, fragmentary view, in section, showing the distal end of a thermotherapy probe of the thermotherapy apparatus of FIG. 1;

FIG. 10 is a simplified representation of a rectal catheter and a transurethral catheter for providing cooling of the rectal wall and the sphincter at different temperatures during thermotherapy treatment;

FIG. 11A illustrates a segmented ultrasound transducer for use as the energy source for the thermotherapy apparatus of the invention;

FIGS. 11B and 11C illustrate an ultrasound element modified to have a portion of its electrode removed to produce focused ultrasound energy;

FIG. 11D illustrates an ultrasound element modified by providing longitudinal slots in the element to produce focused ultrasound energy;

DETAILED DESCRIPTION OF THE PREFERRED EMBODIMENTS

Background

Figure 1A:
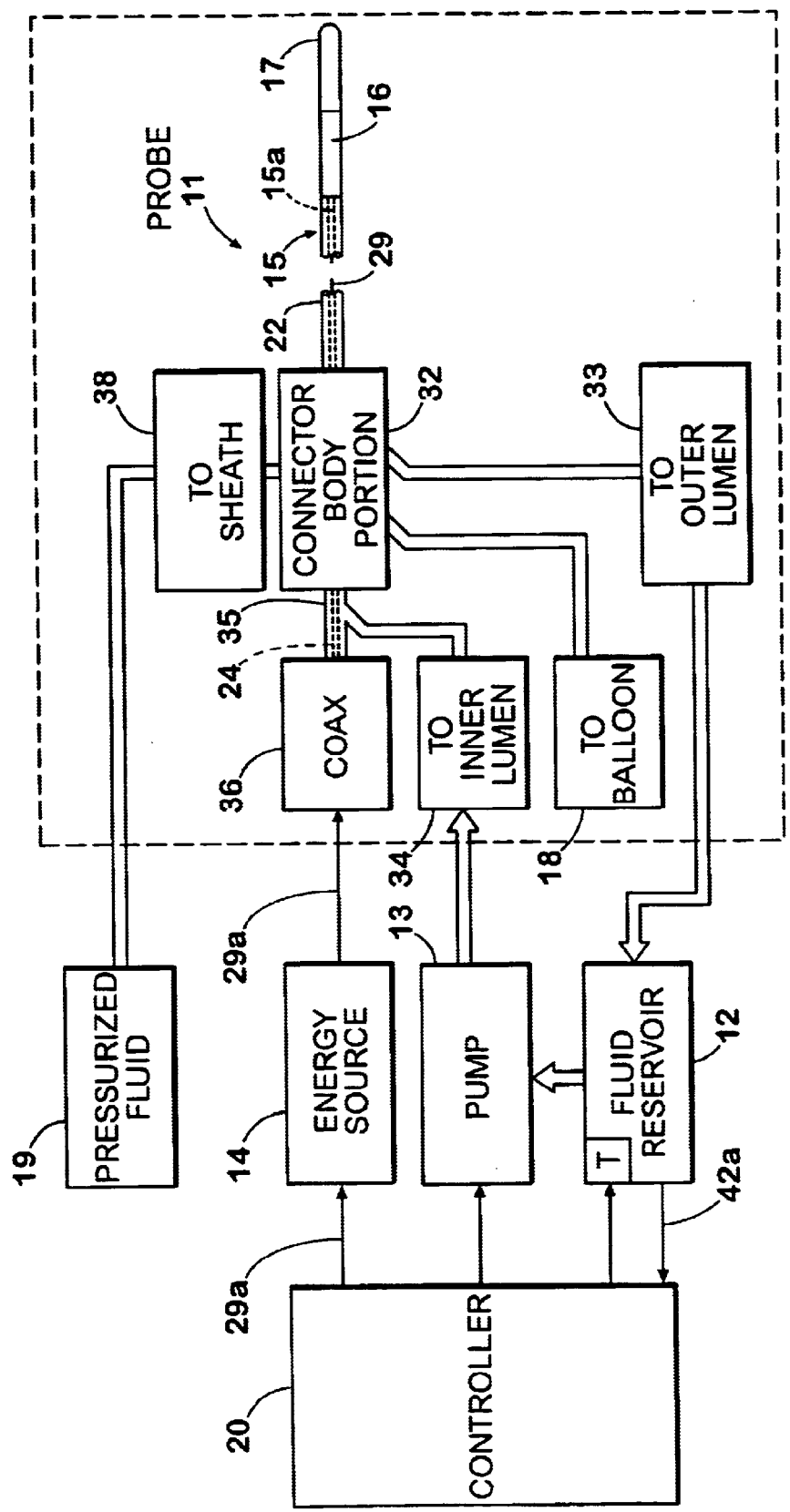
FIG. 1A is a block diagram of thermotherapy apparatus constructed in accordance with one preferred embodiment of the present invention.

The present invention provides an improved apparatus and method suitable for thermotherapy or hyperthermia treatment. Unlike prior art methods and apparatus which limit or prevent thermal energy from reaching non-target tissue, the present invention actually applies controlled thermal energy to non-target tissue. The apparatus and method of the present invention reduces tissue damage and discomfort to a patient by developing a thermotolerance in tissue structures to be protected during thermotherapy or hyperthermia treatment. Throughout this application when referring to "thermotherapy", this terminology shall be meant to include both thermotherapy treatment as well as hyperthermia treatment unless specifically stated to exclude one therapy.

In accordance with the invention, thermotolerance is developed in tissue structures to be protected, hereinafter referred to as non-target tissue structures or non-target tissue, by carefully stimulating the non-target tissues to generate heat shock proteins. Preferably, thermotolerance is developed by heating the non-target tissue for a time and temperature sufficient to cause the production of heat shock proteins in the non-target tissue structures. The preheating is carried out at a temperature, or temperatures, that is sublethal to cells of the non-target tissue structure but is high enough to provoke the building of heat shock proteins. This phase of treatment is referred to as the desensitizing mode. The conditioning treatment causes the formation of heat shock proteins which render the tissue thermotolerant. The tissue structures thus treated or conditioned remain thermotolerant for an extended time period, typically lasting one or two days. On or about the third day following conditioning, the treated tissue structures gradually return to normal.

Because the non-target tissue structures are often more superficial than cancerous tissue to be destroyed, the preheating process can be achieved by using a thermal mechanism which is solely based upon heat conduction. Examples of such thermal mechanisms include heated fluids, and in particular hot water, heating elements driven by DC or low frequency AC current, Peltier elements, or laser Light. When the non-target tissue structures are not superficial, different frequency microwave, RF or ultrasound energy can be used as well.

After heat shock protein formation has been completed, a thermotherapy procedure is carried out to destroy the cancerous tissue, hereinafter referred to as the target tissue. This phase of treatment is referred to as the destructive mode. Because the non-target tissues are protected by heat shock proteins in accordance with the invention, the irradiation of the target tissue can be carried out at higher temperatures than can be used in conventional thermotherapy procedures. This results in more thorough destruction of target tissue, and a thermotherapy treatment process requiring less time than conventional thermotherapy processes, for example, which results in less discomfort and pain for a patient undergoing the treatment. Further, radioflective screens and other complex shielding mechanisms are not necessary for use with the most highly preferred embodiments of the invention.

In contrast to the preheating treatment, the deep neating of target tissue structures is more efficiently achieved by mechanisms where the energy is dissipated in the structure itself by energy conversion from microwave energy. ultrasound energy, or laser energy, for example, into thermal energy by well known relaxation effects and the like, for example. This allows the use of a wide variety of probes including thermotherapy probes similar to known apparatus for application of microwave energy. for example, to enlarged tissue in a practical benign prostatic hyperplasia (BPH) treatment procedure. One such device, commonly referred in as the "cooled" intraurethral probe, includes a microwave antenna that is surrounded by a (usually circulating) fluid, and is adapted to be inserted into a patient transurethrally.

Thermotherapy Apparatus

Referring now to the drawings, and in particular to FIGS. 1A and 1B, thermotherapy apparatus constructed in accordance with one preferred embodiment of the invention is indicated generally at 10 in FIG. 1A. The thermotherapy apparatus includes a thermotherapy probe 11, shown in detail in FIG. 1B, a source or reservoir of a fluid 12, and a pump 13 for circulating the fluid through the thermotherapy probe. The thermotherapy apparatus 10 further includes an energy source 14 and an applicator medium 15 having an applicator portion, indicated generally at 15*a*, located within the probe. The applicator portion 15*a* is driven by the energy source 14 for radiating energy for causing heating of target tissue. A controller 20. is coupled to components of the thermotherapy apparatus 10, including the fluid reservoir 12, the pump 13, the energy source 14, for controlling the operation of these components of the thermotherapy apparatus 10.

One function of the thermotherapy probe is to be at the applicator portion 15*a* in the proximity of the target tissue to be destroyed by thermotherapy treatment. In one preferred embodiment, the thermotherapy probe 11 can include an anchoring balloon 16 near its distal end 17 for use in anchoring the distal end of the probe at a predetermined location within a patient's body to locate an applicator portion 15*a* proximal to the target tissue. The thermotherapy apparatus 10 can include a sealable inflation tube 18 in fluid communication with the interior of the anchoring balloon 16 at the distal tip of the thermotherapy probe 11, to 10 facilitate inflation of the anchoring balloon 16, such as by blowing air into anchoring balloon through the inflation tube 18 in the known manner. The anchoring balloon 16 can provide additional anchoring force, in the manner of a conventional Foley catheter for example. It will be apparent, however, to one skilled in the art that mechanisms other than the conventional anchoring balloon can be used in conjunction with the thermotherapy probe disclosed herein to provide anchoring force for locating the radiation source at the desired location within the patient's body.

Referring additionally to FIG. 2, the thermotherapy probe 11 preferably includes an outer lumen 22, an inner lumen 24, and a sheath 26. The inner lumen 24 is located within the outer lumen 22 so that their axes are substantially coextensive. The outer lumen 22 and the inner lumen 24 can comprise a variety of materials including extruded plastics, but are preferably fabricated from a conventional material such as polyethylene terephthalate. This material should preferably have properties resulting in the lumens 22 and 24 being substantially nondistensible, and therefore become substantially rigid when inflated with fluid (liquid or gas) being introduced into input ends and of the lumens 22 and 24, respectively. The anchoring balloon 16 can be secured to the distal tip of the outer lumen 22 in the conventional manner.

One highly preferred form of this invention, the sheath 26 is an inflatable structure. Moreover, the sheath 26 is adapted to be inflated after the distal end of the probe has been positioned at the proper location in the patient's body. When inflated, the sheath 26 renders the thermotherapy probe 11 substantially rigid. This rigidity gives rise to several features including the ability to straighten the body passage and surrounding organs into which it is inserted as will be shown. Further, the nondistensible, inflated sheath 26 can securely retain the thermotherapy probe 11 in a desired location while inserted.

Referring to FIG. 1B, which is a plan view of the thermotherapy probe 11, and to FIG. 1A, which shows elements of probe 11 in block diagram form, the thermotherapy probe 11 preferably includes a connector body portion 32 having a first tube connector 33 in fluid communication with the interior of the outer lumen 22 and being adapted for connection to the fluid reservoir 12. A second tube connector 34 is in fluid communication with the interior of the inner lumen 24 and is adapted for connection to the pump 13. In addition, the connector body portion 32 includes an inlet 35 on which is mounted the coaxial connector 36. A further tube connector 38 is in fluid communication with the interior of the sheath 26 and is adapted for connection to a source of fluid under pressure 19, such as air of water, for inflating the sheath.

Heating fluid from the fluid reservoir 12 is pumped through the thermotherapy probe during the desensitizing mode of the treatment. The fluid reservoir 12 can include suitable temperature controls 12a which allow precise control of the temperature of the fluid contained in the reservoir. Moreover, the temperature controls 12a allow the temperature of the fluid in the reservoir to be adjusted to different values during the treatment. Preferably, the temperature controls 12a are operated under the control of the controller 20. However, the temperature controls can be adapted for manual operation.

Figure 3:
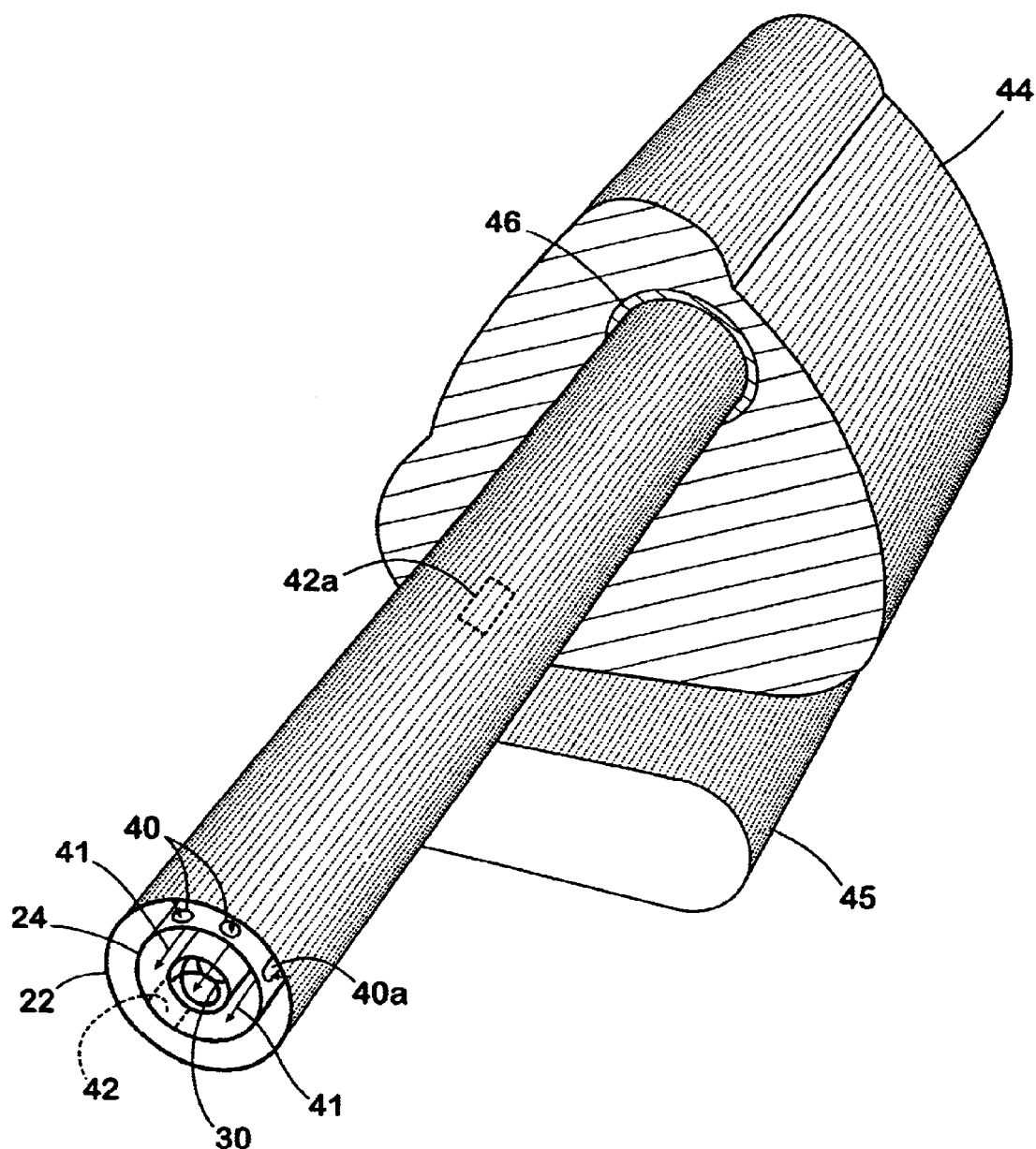
FIG. 3 is an enlarged, fragmentary, isometric view showing the thermotherapy probe inserted transurethrally into the prostate gland of a patient.

In one preferred embodiment, the inner lumen 24 is maintained in fluid communication with the outer lumen 22. To this end, a plurality of holes 40 are provided at the outlet or distal end of the inner lumen 24 (see FIG. 3) communicating the interior of the outer lumen 22 with the interior of the inner lumen 24. This allows heating fluid introduced into the inner lumen 24 during the desensitizing mode to be communicated to the outer lumen 22. The heating fluid exits the inner lumen 24 through the holes 40 and enters the outer lumen 22 along flow paths 41 as shown in FIG. 3, for example.

In addition, in one preferred embodiment, the inner and outer lumens of the thermotherapy probe 11 are used to permit cooling fluid to be pumped through the interior of the inner lumen 24 during the destructive mode of the treatment. Prior to the start of the destructive mode of treatment, the temperature of the fluid contained in the fluid reservoir 12 can be decreased to the desired temperature, under the control of the controller 20, for example. In this embodiment, the cooling fluid introduced into the inner lumen 24 can exit the inner lumen 24 through the holes 40 and enter the outer lumen 22 along the flow paths 41 (FIG. 3).

The applicator medium 15 extends within the inner lumen 24. In the embodiment shown in FIG. 2, the applicator medium 15 comprises a conductor portion 29. The applicator portion 15a of the applicator medium 15 comprises a helical microwave antenna 30. The antenna 30 is mounted on the distal end of a conductor 29, the proximal end of which is connected to a suitable coaxial connector 36 (FIG. 1B) which facilitates connection of the antenna 30 to the energy source 12 by way of a coaxial cable 29a in the known manner.

The application portion 15a is adapted to be inserted into the inner lumen 24 and advanced to a location near the distal end of the probe. The conductor 29 and the antenna 30 are adjustably positioned within the inner lumen. This allows the applicator portion, including antenna 30, to be moved axially within the inner lumen until the antenna 30 is properly positioned relative to the target tissue. Then the conductor portion 29 is secured to maintain the applicator portion 15a at the proper location.

A temperature sensor 42 can be embedded in the inner lumen 24 near the distal tip thereof. Alternatively, a temperature sensor 42a can be provided along the outer lumen 22 midway along the applicator portion 15a of the energy source as shown in FIG. 2. The temperature sensor 42 enables monitoring of the temperature of the heating fluid during the desensitizing mode. In addition, the temperature sensor 42 enables monitoring of the temperature of the cooling fluid during the destructive mode. In both cases, the temperature sensor provides feedback to the controller 20 to allow adjustment in the heating fluid during the desensitizing mode, and in the amount of microwave power being emitted and/or the temperature of the cooling fluid to prevent overheating of the non-target tissue during the destructive mode. Alternatively, a different temperature sensor can be used in providing an output indicating the temperature of the non-target tissue during the desensitizing and/or destructive mode.

Process

As a non-limiting example, use of the improved thermotherapy apparatus 10 for the treatment of benign prostatic hyperplasia will be described and shown herein.

Figure 4:
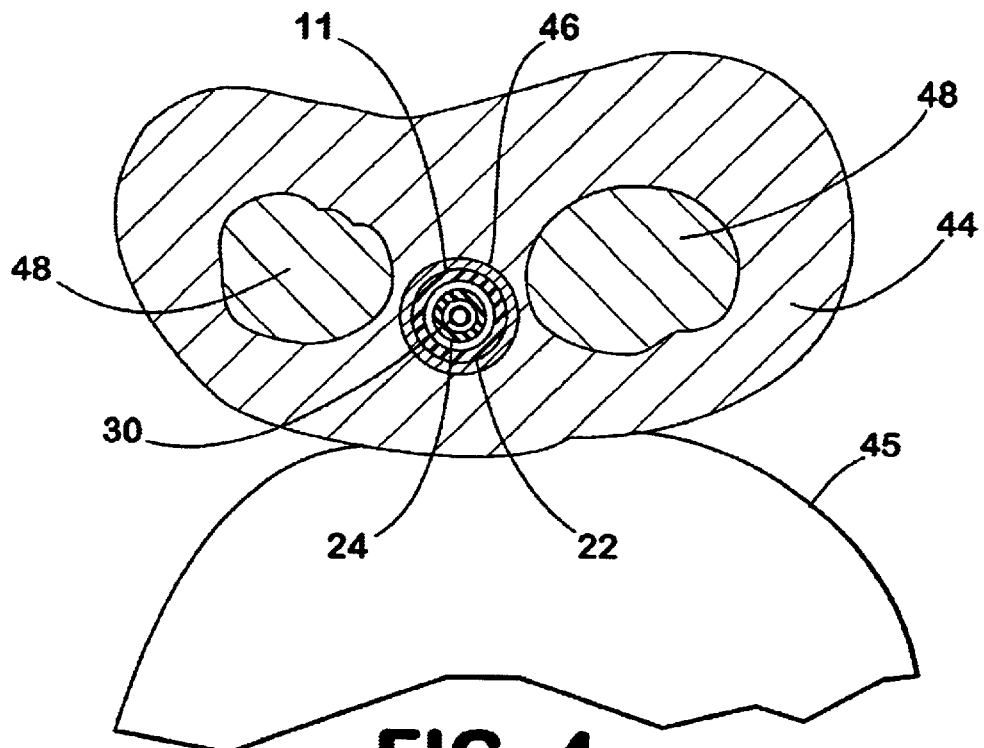
FIG. 4 is an end view showing the thermotherapy probe inserted transurethrally into the prostate gland of a patient.

Referring to FIGS. 3 and 4, the thermotherapy probe 11 is shown inserted transurethrally into the human prostate gland 44. As shown in FIG. 4, the rectal wall 45 can be located dose to the urethra 46 as the distal end of the probe 11 passes through the prostate gland 44.

Figure 5:
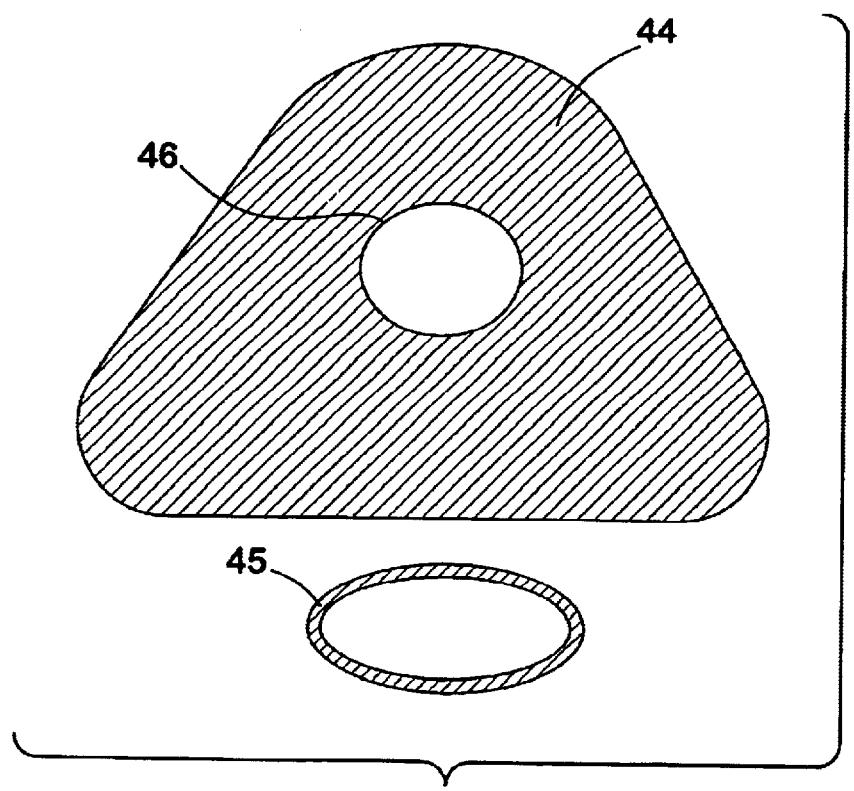
FIG. 5 is a simplified representation, in cross-section, of a normal prostate gland, urethra and rectum.
Figure 6:
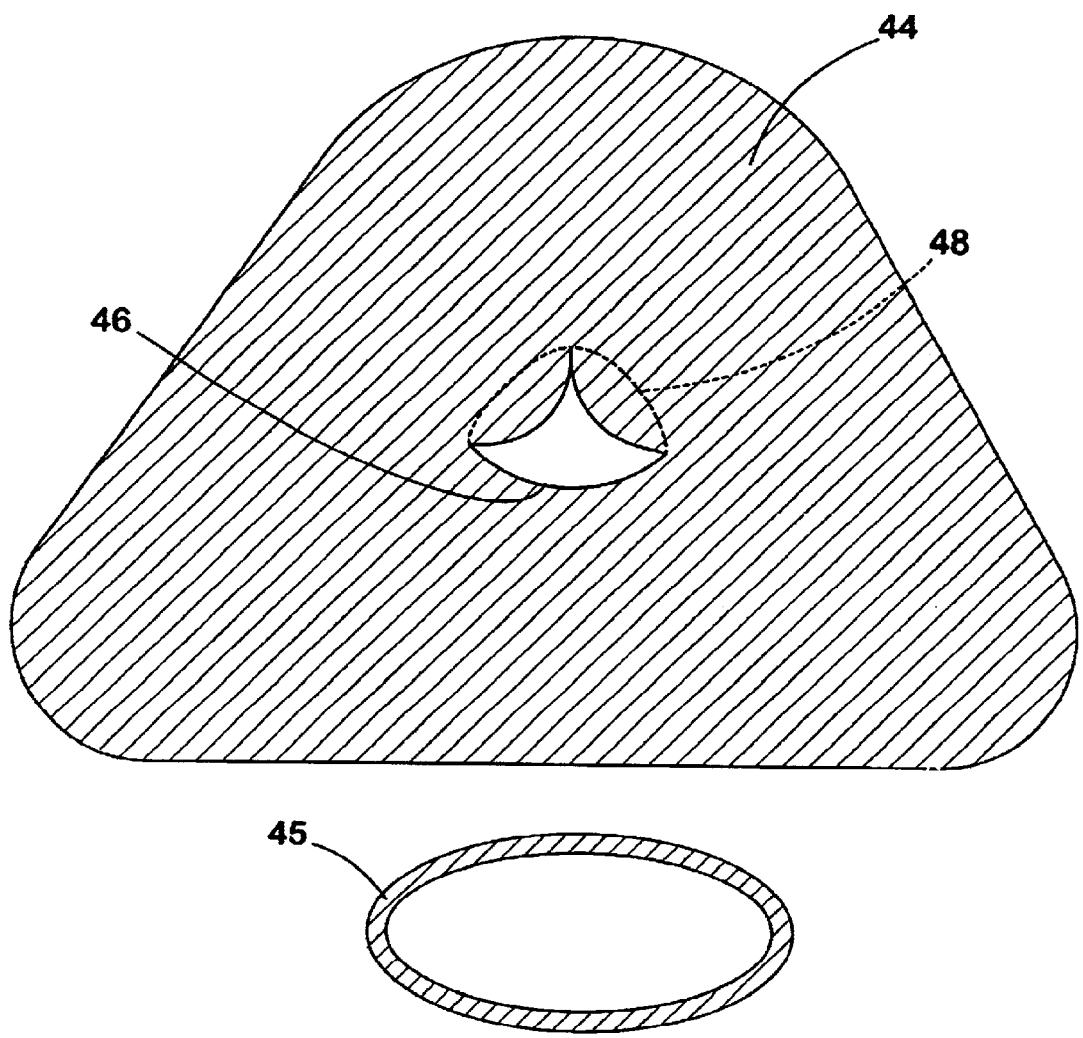
FIG. 6 is a view similar to FIG. 5 and illustrates an enlarged prostate gland impinging upon the urethra.
Figure 7:
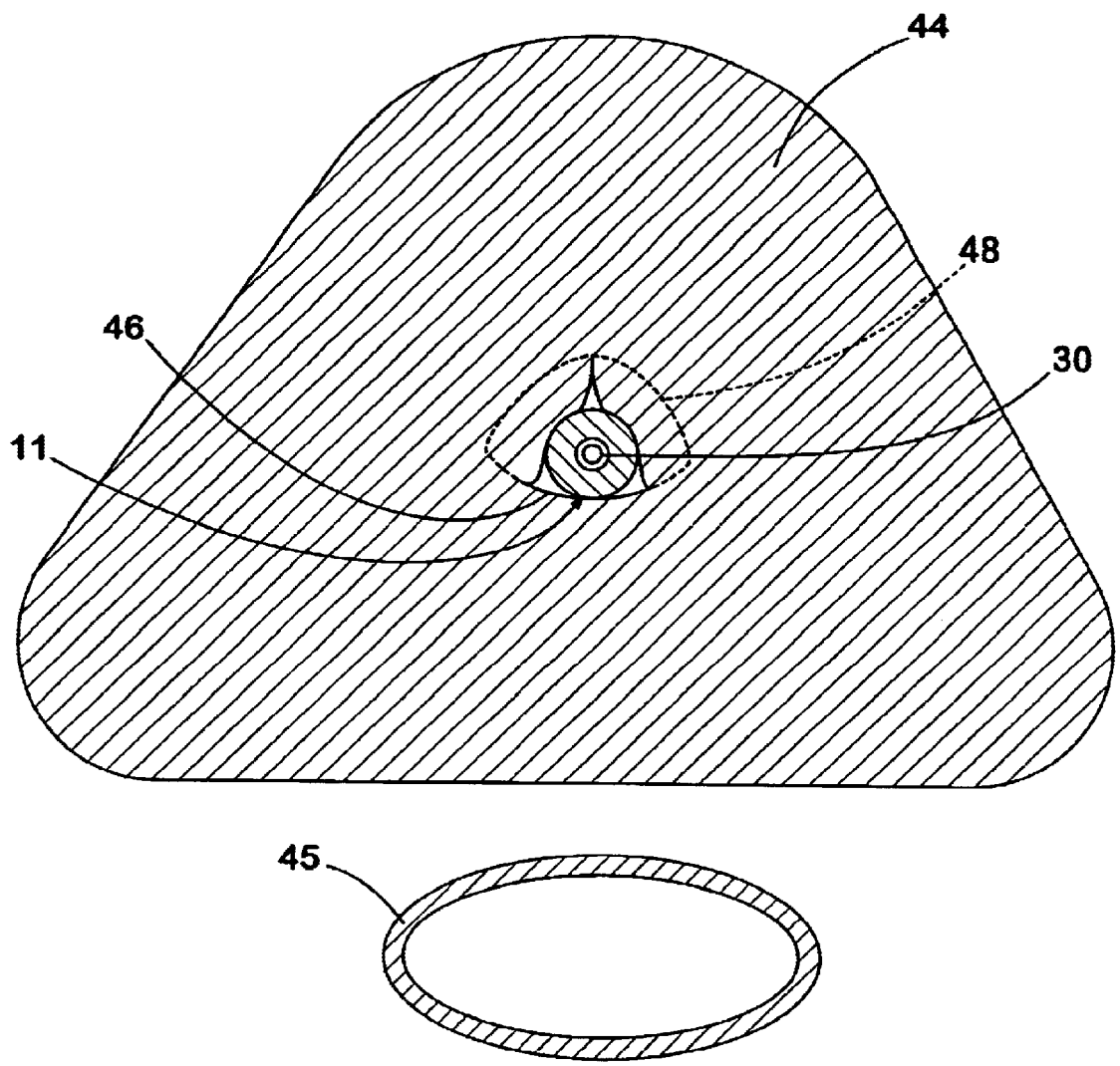
FIG. 7 is a view similar to FIG. 6 and illustrates an enlarged prostate gland with a thermotherapy device of the present invention inserted therein.

Digressing, with reference to FIGS. 5–7, FIG. 5 is a simplified representation of a cross section of a normal prostate gland 44, urethra 46 and rectal wall 45. FIG. 6 is a simplified representation of an enlarged prostate gland impinging on the urethra 46. FIG. 7 illustrates the enlarged prostate gland 44 of FIG. 6 and with the thermotherapy probe 11 inserted therein, transurethrally.

The rectal wall 45 is Located relatively close to the urethra 46. As shown in FIGS. 6–7. the transitional zone 48 of the prostate gland 44 is the primary source of tissue impinging upon the urethra 46. This impingement causes difficult urination due to the restricted diameter of the urethra 46. This can cause serious kidney problems and extreme discomfort. The structure of the present invention enables application of the radiation to the prostate gland 44 to be preferentially directed to the diseased tissue (such as, the transitional zone 48 in FIG. 6), giving rise to more effective treatment with thermotherapy, while also preventing tissue damage, such as damage to the rectal wall 45.

Referring again to FIGS. 3 and 4. the thermotherapy probe 11 is inserted into the patient transurethrally for locating the energy source in the proximity of the target tissue 48. The thermotherapy probe 11 is inserted a distance such that the anchoring balloon 16 (FIG. 2) is located in the bladder 50 (FIG. 13A) before being inflated. The anchoring balloon is inflated with water or air through the tube connector 18 (FIG. 13A) and pulled back to rest against the bladder neck 51 in the conventional manner, So that the distal end of the thermotherapy probe is anchored.

Then. the conductor 29 extending within the inner lumen 24 is adjusted to Locate the helical microwave antenna 30 at the location to be generally aligned with the target tissue 48 (FIG. 7). Proper positioning of the antenna can be confirmed using imaging techniques as is known in the art. The conductor can then be fixed in this position.

Referring additionally to FIG. 1A, the heating fluid from the fluid reservoir 12 can be introduced into the inner lumen 24 through the tube connector 34 and circulated by pump 13, the fluid being conducted to the interior of the outer lumen 22 through the openings 40 (FIG. 3). Various pressures and flow volumes of the heating fluid can be provided to the thermotherapy probe 11.

As has been stated above, the desensitizing mode includes a high temperature period of a relatively short time duration, which is the trigger or initializing period, followed by a lower temperature period, or development period, of a longer duration, during which heat shock proteins are produced in the non-target tissue structures. To achieve the desired protection effect, the preheating fluid that is circulated through the lumens 22 and 24 during the trigger period is warmed up to a "preheat value". The preheat value can be in the range of approximately 41° C. to 50° C., and more specifically about 41° C. to 45° C. In one preferred embodiment, the value is 42° C. The preheating is applied for sufficient time as to allow for achieving heat shock protein production during the desensitizing mode phase of the treatment. By way of example, the duration of the trigger or initializing period can be from about fifteen minutes to about four hours depending upon the temperature, and preferably for a temperature of 42° C., and preferably is in the range of about fifteen minutes to about thirty minutes.

Then, the temperature of the heating fluid is lowered to a value in the range of about 10° C. to 43.5° C., for example, and preferably about 37° C., for example, for the development period. The duration of the development period is preferably in the range of about four hours to about eight hours, and more preferably about six hours to six and one-half hours. It is apparent that one preferred temperature for the development period is 37° C., or approximately body temperature. Thus, at the end of the trigger period, which can be as short as fifteen minutes, the non-target tissue that has been subjected to preheating, can be returned to body temperature by lowering the temperature of the heating fluid. When body temperature is reached, the thermotherapy probe 11 can be removed from the patient undergoing treatment. The patient can be allowed to rest for the duration of the development period. At the end of the development period, the thermotherapy treatment can be carried out.

As has been stated above, the duration of the decay period can be three to four days. depending on the temperature and duration of the trigger period and of the development period. By the end of the decay period, thermoresistance has worn off and the treated tissue essentially has returned to its normal condition. Thus, the destructive portion of the thermotherapy treatment is carried out so as to be completed well in advance of the end of the decay period.

Figure 8:
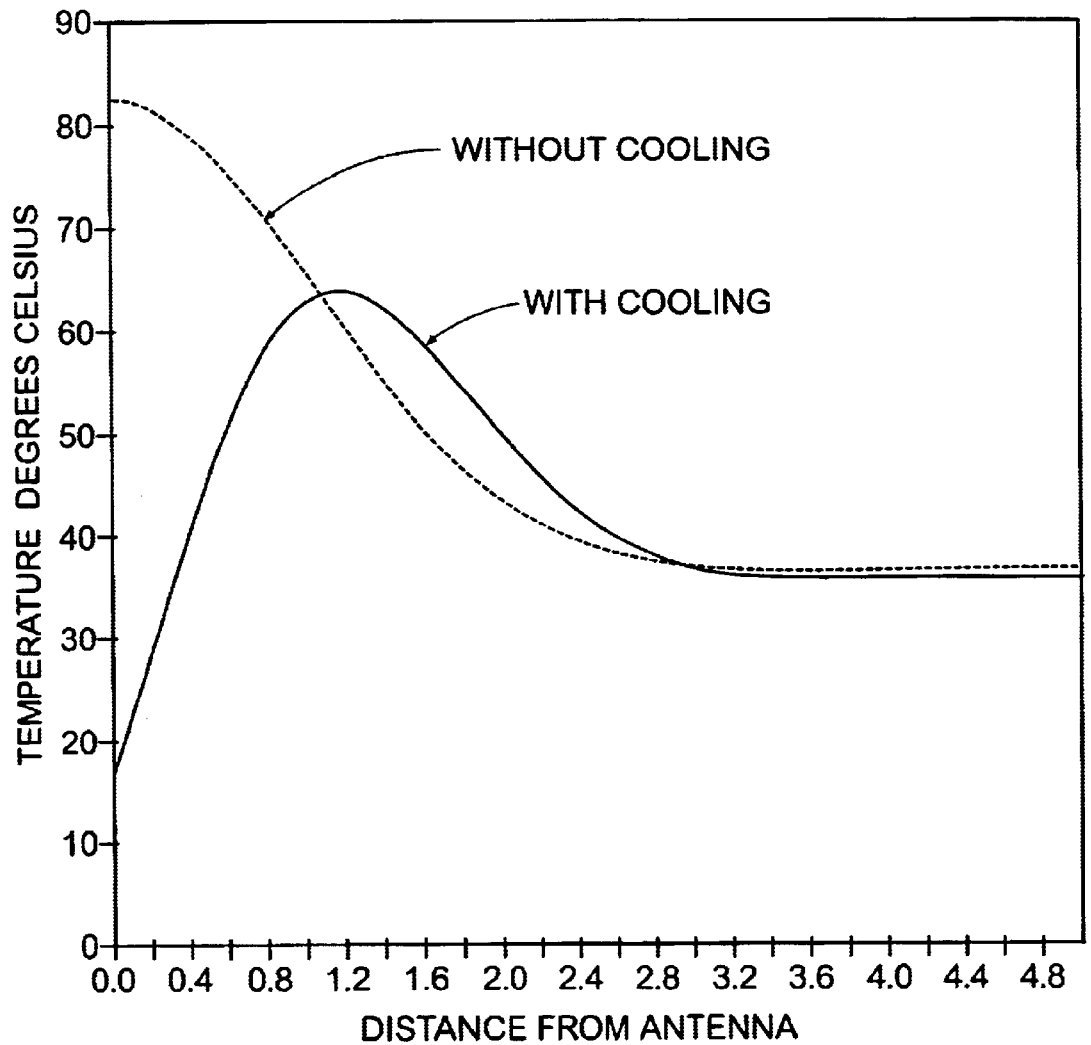
FIG. 8 is a graph illustrating temperature as a function of distance from the energy source with cooling and without cooling.

Reference is now made to FIG. 8, which is a graph illustrating temperature as a function of distance from the energy source. When the preheating is completed and the heat shock proteins have been formed in the non-target tissue structures, the microwave energy is applied. The microwave energy forms the well known temperature profile, shown in FIG. 8, during the destructive mode phase of the procedure for a thermotherapy procedure that employs cooling, as represented by the solid line. For purposes of reference, FIG. 8 also shows a temperature profile, represented by the dashed line, for a thermotherapy procedure without cooling. As can be seen by comparing the two temperature profiles, there is a considerably higher temperature in the region between the energy source and the target tissue, when cooling is not used during the destructive mode. In contrast, when controlled cooling is used, the temperature gradually increases as a function of distance from the source of energy, with the temperature peaking in the proximity of the target tissue. In the treatment of benign prostatic hyperplasia, experiments have shown that exceptional cooling can be provided from applying pressures of 30 to 265 pounds per square inch at circulating volumes of 10 to 100 milliliters per minute. It will be apparent to one skilled in the art that different cooling methods, cooling fluids and cooling fluid volumes and pressures can be utilized effectively.

It is well known that high temperatures in the rectal wall can be caused by microwave treatment of benign prostatic hyperplasia and can severely limit the duration and effectiveness of the treatment. As has been discussed previously, thermotherapy requires higher temperatures generally to be maintained at the abnormal tissue compared to conventional hyperthermia treatments. Accordingly, protection of the rectal wall is even more critical then when performing a hyperthermia treatment.

The present invention allows the thermal power used in the destructive mode to be increased without increasing adverse effects. This allows for faster treatment (less time consumption) and a more efficient procedure. In cancer treatment, the additional "headroom" that is afforded by use of a thermal dose that is higher than the thermal dose possible when using conventional thermotherapy techniques, affords more certainty of the destruction of all malignant cells. As has been pointed out above, using prior art techniques, if tissue structures existed that had to be protected from the high temperatures associated with the thermotherapy procedures, heating of tissue with microwave energy had to be limited such that the temperature dose to the energy source, such as the microwave antenna 30 in the embodiment illustrated in FIG. 2, did not exceed about 43.5° C. to 45° C. The requirement that temperature be limited to such level limits the maximum thermal dose that can be applied to the insert tissue structures, which can render the therapy insufficient in some cases.

Figure 9:
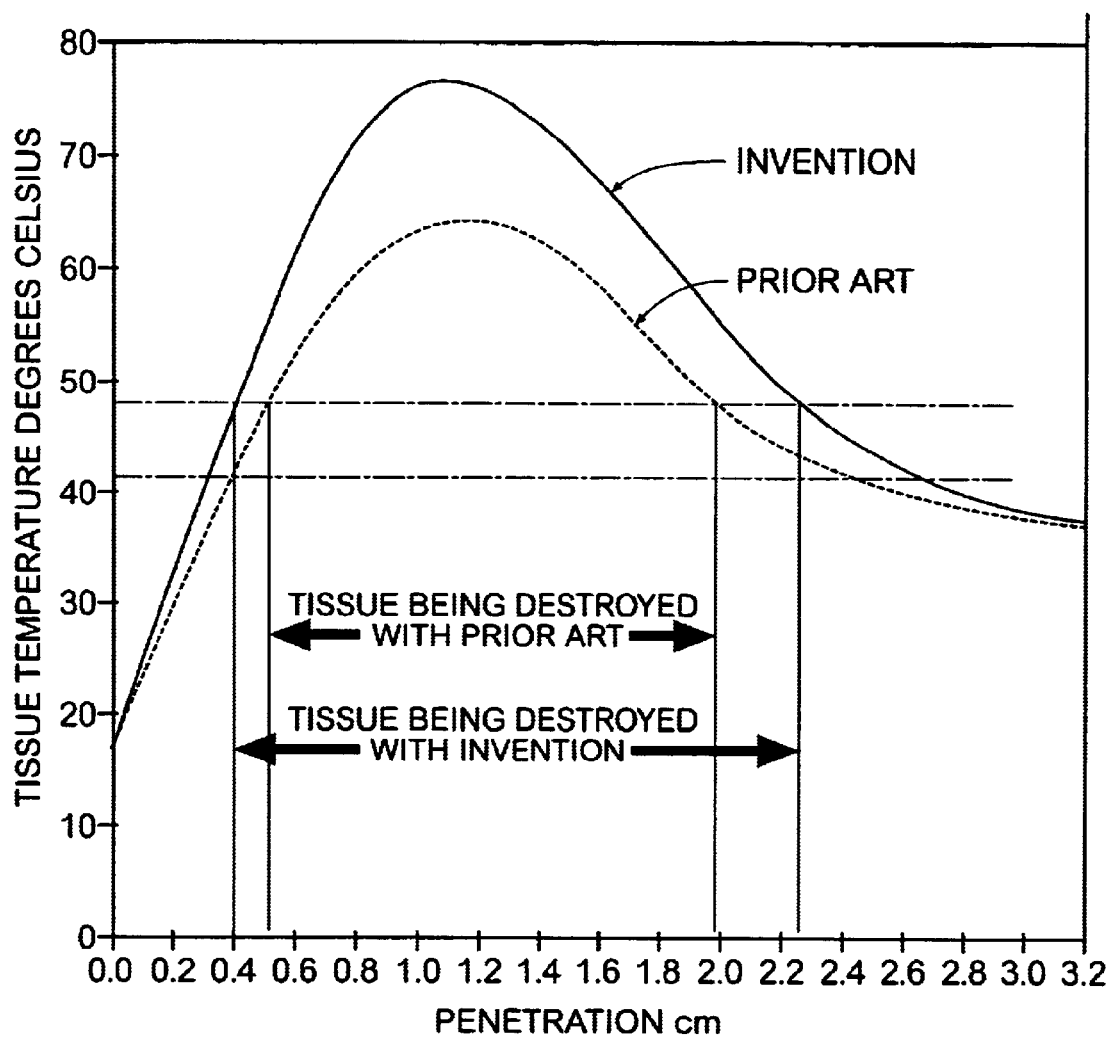
FIG. 9 is a graph illustrating temperature as a function of distance from the energy source for conventional thermotherapy procedures and the thermotherapy procedure provided by the invention.

Referring to FIG. 9, there is shown a graph illustrating temperature as a function of distance from the energy source. In FIG. 9, temperature at a given depth of tissue for conventional thermotherapy methods is represented by the solid line, and temperature at a given depth of tissue for the thermotherapy method provided by the invention is represented by the dashed line. As can be seen, for a given depth of penetration of the microwave energy, a higher temperature can be provided at the target tissue using the method of the invention. Using prior art methods, the applied temperature at the location of the target tissue has to be limited to about 43.5° C. whereas the invention, in one example, can heat target tissue to a temperature of 45° C.

Protection of Rectal Wall

Referring again to FIG. 7, because the thermotherapy probe 11 radiates energy in a symmetrical pattern during treatment, this results in treatment being relatively close to the rectal wall 45. The microwave antenna 30 in the applicator 15 typically produces a cylindrical energy field which is symmetric about the antennas longitudinal axis. High temperatures for the rectal wall 45 can arise from straightforward application of energy from such a cylindrical source and can limit the duration and effectiveness of the treatment of the transitional zone (enlarged tissue) 48 of the prostate gland 44.

Tissue structures, such as the rectal wall, that have to be protected generally are more superficial than the tissue structures to be destroyed by the thermotherapy process. In accordance with the invention, the preheating process can be achieved by using hot water as the thermal mechanism which is solely based upon heat conduction. Alternatively, other thermal mechanisms, such heating elements driven by DC or low frequency AC current, Peltier elements, etc., or low level laser light that is limited to a minor penetration into tissue, can be used. The preheating for inducing the formation of heat shock proteins in the rectal wall tissue affords a degree of protection to the rectal wall from the high temperatures produced during the destructive mode.

Alternatively, to provide increased protection for the rectal wall, the thermotherapy probe, and in particular, the applicator portion thereof, can be constructed to provide asymmetrical application of energy during the destructive mode. One example of a thermotherapy device which provides asymmetrical application of energy is disclosed in U.S. Pat. No. 5,733,316.

Referring to FIG. 10, a special application is the destruction of benign and/or malign prostatic tissue wherein the rectum 45 and sphincter 47 have to be saved. In the desensitizing mode, the rectum 45 is warmed by a warming medium, such as warm water, that is contained in a rectal catheter 49. The sphincter 47 is warmed by a separate warming medium, such as warm water, that is introduced into probe 11 that is inserted transurethrally into the patient. The warm water contained in the rectal catheter and/or the transurethral catheter can be circulated through the catheter(s).

Alternative Cooling Methods

A number of alternative cooling methods can be utilized with this structure. For example, referring in FIGS. 1–3, the cooling fluid entering the inner lumen 24 (which does not have openings 40) can be allowed to travel the full length of the inner lumen 24 and back the full length again whereupon it exits through the inner lumen outlet. In this embodiment, a separate cooling fluid reservoir and pump are utilized to circulate a cooling fluid to the inner lumen 24. This embodiment allows the inner lumen 24 to be kept at a significantly lower temperature (or different temperature) than the outer lumen 22.

Alternatively, the cooling fluid can be introduced into the outer lumen 22. The cooling fluid entering the outer lumen 22 can be allowed to enter the inner lumen 24 through a series of holes 40 or a slot 40a (FIG. 3), or other such openings, disposed along the adjacent perimeter of the outer lumen 22 and the inner lumen 24. This equalizes the temperature of the fluid being circulated through the two lumens 22 and 24 and provides uniform cooling to the tissues within which the thermotherapy device 11 is inserted.

Alternative Energy Sources

In the foregoing embodiments, the microwave energy is introduced by way of an antenna that is inserted into a probe that is inserted transurethrally into the body of the patient being treated. However, the microwave energy can be introduced in other ways. For example, in the destructive mode, the microwave energy can be applied using interstitial antennas that are introduced transperineally. Further, it will be apparent to one skilled in the art that heat or radiation sources other than the microwave antenna described for energy source can be equally suitable for proposed treatments (thermotherapy or hyperthermia, though for the purposes of determining the scope of the claims "thermotherapy" is considered to include hyperthermia Treatment).

Ultrasound

In another embodiment, an ultrasound transducer can be used to deliver the radiant energy as the energy source. The ultrasound transducer can be driven at high frequencies in the desensitizing mode and low frequencies in the destructive mode. If the ultrasound elements used are configured as closed tubes, the resultant focusing of energy radiated by the elements results in a toroidal zone of maximum power deposition.

Figure 12:
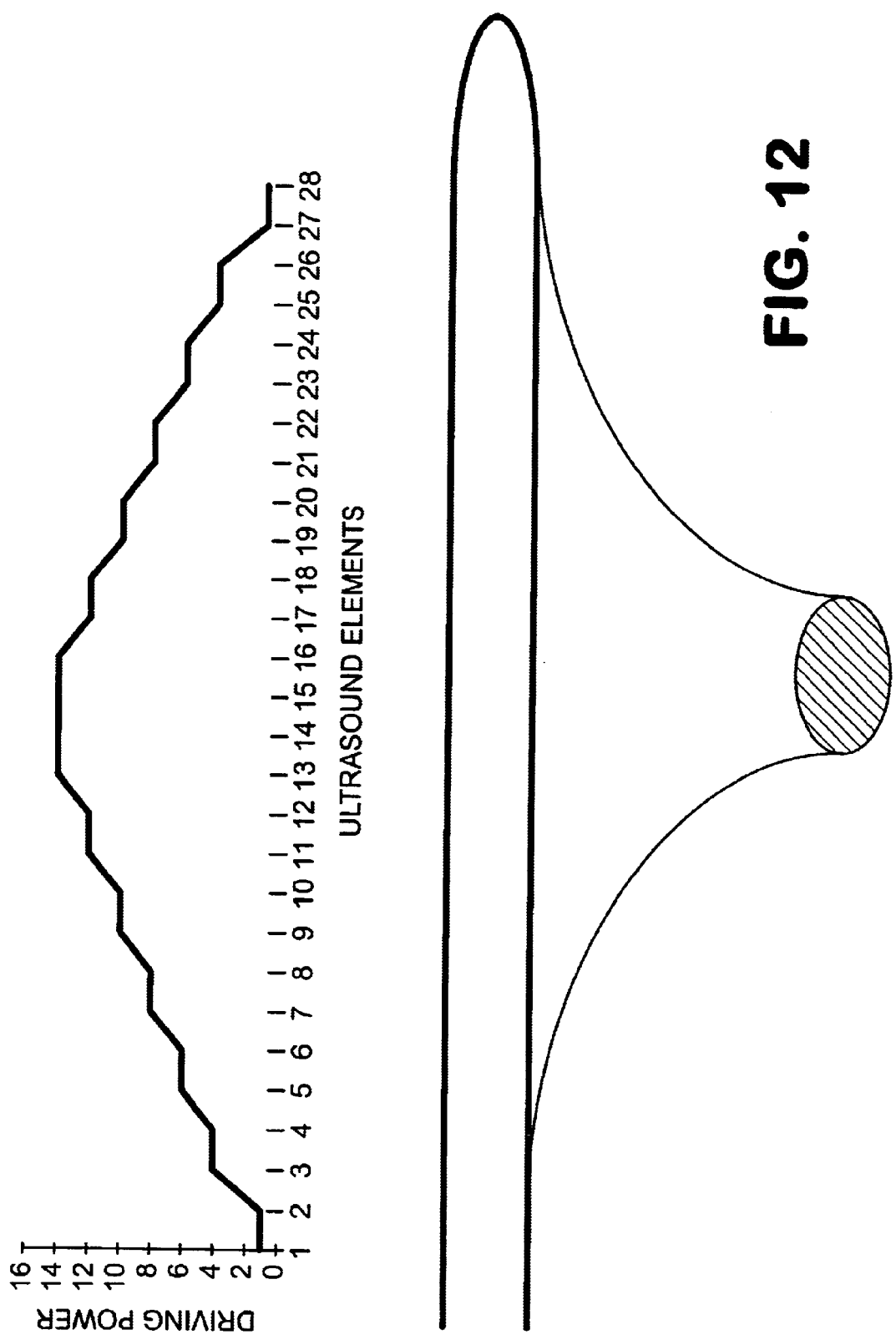
FIG. 12 is a simplified representation of the energy levels produced by the transducer of FIG. 11A.

Referring to FIG. 11A, there is shown a simplified representation of an ultrasound transducer 60, segmented to define a plurality of elements. In one embodiment the ultrasound transducer includes five elements 61–65. The transducer 60 is positioned relative to target tissue such that the zone of highest focusing is located at the target tissue. The driving power is represented by the number of elements, as shown in FIG. 12.

Alternatively, the driving distribution can be changed to shift the power zone to ensure proper coupling, by using a phased array-type ultrasound probe adapted for insertion into a catheter with or without fluid circulation.

Moreover, the ultrasound transducer can be modified to produce focused ultrasound. If it is desired to save parts of the tissue structures, such as the rectal region, one or more of the ultrasound elements can be modified to limit the amount of ultrasonic energy that is directed towards the rectal region during the radiation procedure. For example. as shown in FIGS. 11B and 11C, an ultrasound element 70 has a portion of its electrode 72 removed. Alternatively, as illustrated in FIG. 11D, an ultrasound element 74 is modified by providing longitudinal slots 76 in the element at the side facing the rectal region. As it is known in the art, to build up focused ultrasound transducers, focusing may be used in the destructive mode to enhance targeting at well-circumscribed structures. Examples of focused ultrasound transducers are disclosed in U.S. Pat. No. 5,733,315.

Laser Light

In another embodiment, laser energy can be used. One such structure, using a laser Light guide, as disclosed in U.S. Pat. No, 4,878,725 (Hessel, et al.), is a satisfactory energy source when used in conjunction with a laser-transparent lumen material.

Another practical treatment apparatus uses laser light of different frequencies. The laser light at different frequencies can be supplied by using a plurality of light tubes contained within the same catheter. The wavelength of the first treatment, in the desensitizing mode, is chosen such that the penetration of energy is only superficial, from 2 to 5 millimeters. The laser energy is limited to temperatures not exceeding lethal Limits of cells, such provoking the building of heat shock proteins. The wavelength of the second treatment, in the destructive mode, is adjusted to provide the desired maximum penetration. It is possible to apply an additional cooling to the surface. An example of a laser light energy source is illustrated in FIG. 14. The laser light source includes a source of laser light and first and second light tubes.

Variations in Cooling

In another form of the invention. a radioreflective form of the fluid can be flowed through the inner lumen 24 to effectively screen the rectal wall from high intensity microwave energy. Another variation on this concept is the use of radiation absorptive fluids in the inner lumen 24 to screen the rectal wall 45. Another variation is the use of a radioreflective or radiation absorptive substance to form a lining in at least a portion of a cooling chamber to provide the desired screening effect.

In the form of the invention using a laser device as the energy source, a light reflective or absorptive fluid or substance can be used in (or on) a cooling chamber to effectively screen the rectal wall from high intensity energy. The form of the invention using an ultrasound type of energy source can utilize a sound reflective or absorptive fluid or substance in (or on) a cooling chamber for high intensity energy screening purposes.

Straightening of the Urethra

Figure 13A:
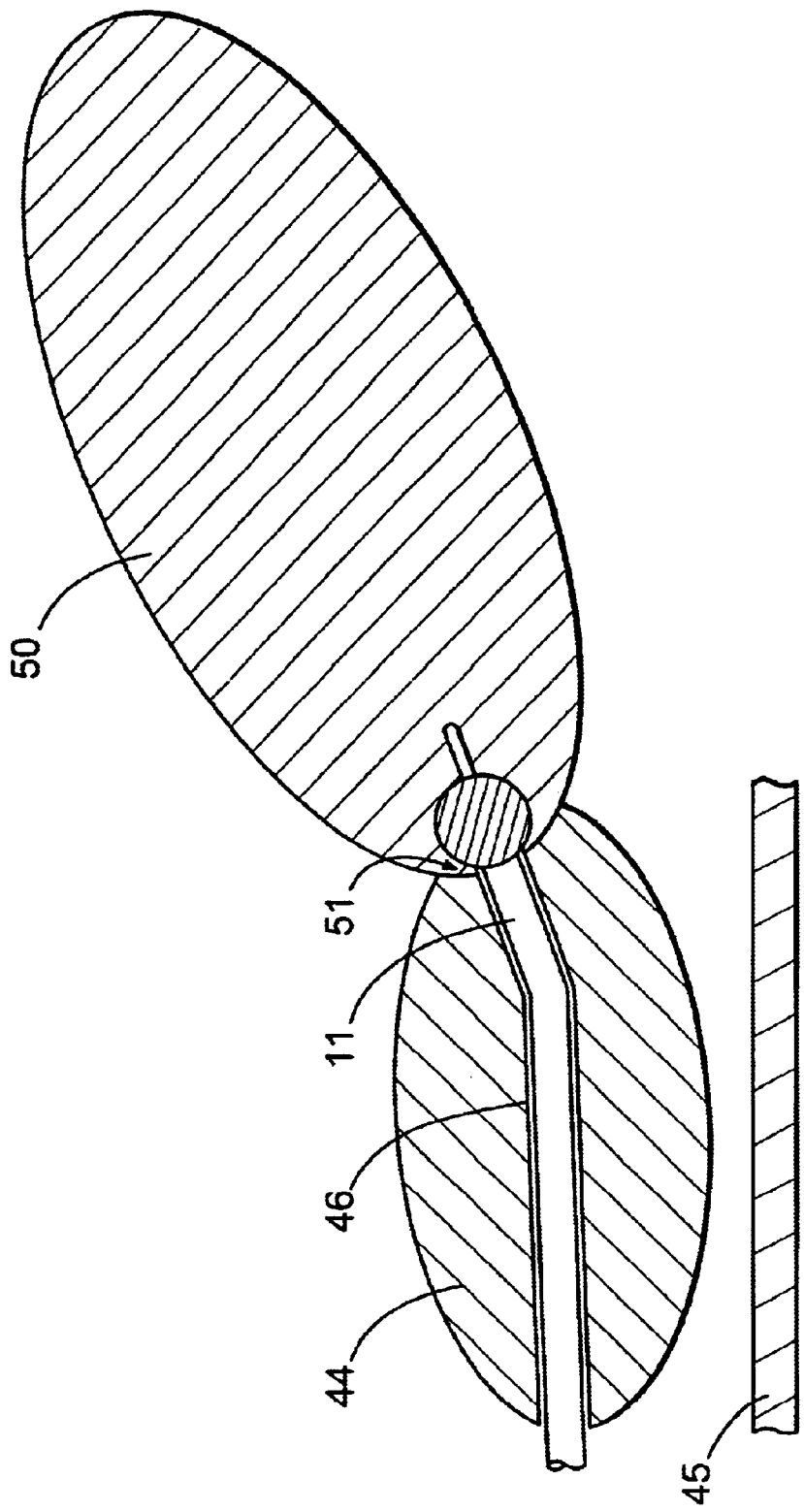
FIG. 13A is a simplified representation of a naturally curved prostate gland.
Figure 13B:
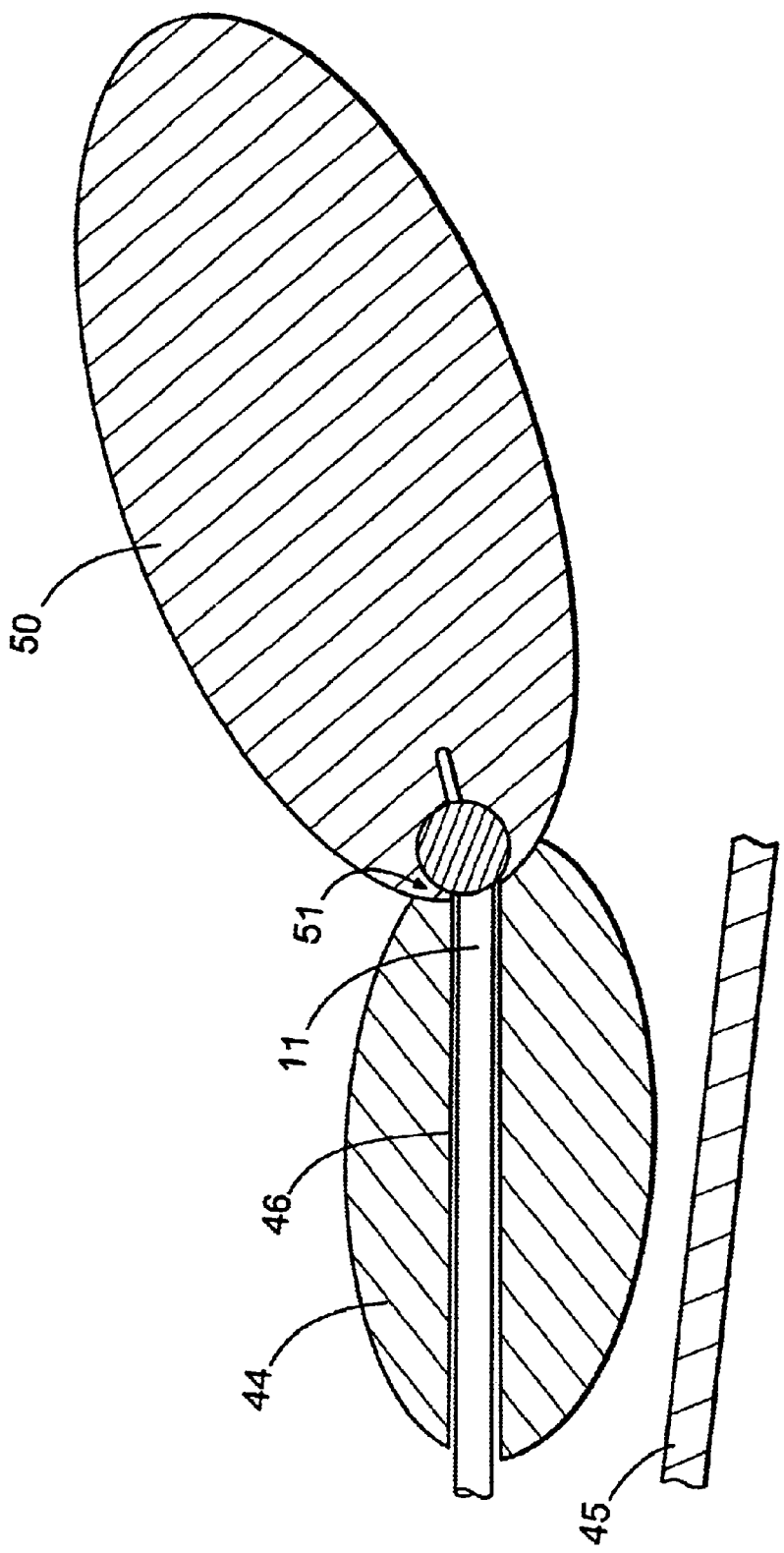
FIG. 13B a view similar to FIG. 13A and illustrating the prostate gland straightened by a thermotherapy probe provided by the invention.

A non-limiting example of this feature of the invention shown in FIGS. 13A and 13B is the straightening of the urethra 46 and prostate gland 44 in the thermotherapy treatment of benign prostatic hyperplasia. The lumens 22 and 24 and the outer sheath 26 can be constructed in a manner to allow selective extension and expansion of the probe. As shown in FIG. 13A, the urethra in a normal prostate gland 44 exhibits a curved portion having an angle of approximately 30°. This curved portion of the prostate gland 44 is straightened to the configuration shown in FIG. 13B when the sheath 26 is pressurized to about thirty pounds per square inch with fluid. This straightening action permits treatment of a well-defined geometry, providing a more effective treatment of the prostate gland 44. Such a symmetrical shape allows use of a more predictable energy treatment field. Further, this element of the invention enables the thermotherapy device 11 to be securely anchored by friction along an extended longitudinal expanse of the walls of the thermotherapy device 11, rather than requiring an anchoring balloon along a narrow length or unstable position.

Interstitial Insertion

Yet another embodiment of the invention allows interstitial insertion of the thermotherapy probe 11 for thermotherapy treatment of tissues which are not located in close proximity to normal body openings or channels. In this embodiment, the thermotherapy probe 11 can be inserted into a conventional rigid probe (such as a catheter) that is provided with a pointed insertion tip.

Modifications

The shapes of the lumens 22 and 24 can be modified to provide the desired path length of cooling fluid (and path length of radiation absorber or reflector) seen by energy emanating from the microwave antenna (or other suitable energy source). The cooling fluid can comprise an energy absorber or reflector in enable the clinician to have the ability to construct a desired heating pattern to maximize treatment of disposed tissue and minimize harm to normal tissues.

While preferred embodiments have been illustrated and described, it should be understood that changes and modifications can be made therein without departing from the invention in its broader aspects. Various features of the invention are defined in the following claims.

What is claimed is:

1. A method for protecting non-target tissue structures of a patient's body from unintended damage during thermotherapy treatment of target tissue located adjacent to the non-target tissue structures, said method comprising the steps of:

inserting into the patient's body a thermotherapy probe including inner and outer lumens;

pumping a heated liquid through the inserted thermotherapy probe for heating the non-target tissue structures in a first treatment mode to a first temperature that is sublethal to the non-target tissue structures but is high enough to provoke the building of heat shock proteins in the non-target tissue structures;

positioning an applicator portion of an energy source in at least one of the lumens; and applying radiative energy from the energy source to target tissue for heating the target tissue in a second treatment mode to a second temperature that is high enough to kill a desired cell mass contained in the target tissue.

2. The method according to claim 1, further comprising the step of providing a delay between the first treatment mode and the second treatment mode to allow for sufficient building of the heat shock proteins.

3. The method according to claim 1, wherein the first temperature is in the range of about 42° C. to 50° C. and wherein the second temperature is higher than about 48° C.

4. The method according to claim 1, further comprising the steps of providing a further delay after the second treatment mode, and heating the adjacent structures in a third treatment mode to at least the second temperature, to thereby provide sequenced treatment.

5. The method according to claim 1, further comprising the step of introducing a cooled liquid into the probe during the second treatment mode for cooling the non-target tissue structures in the second treatment mode.

6. The method according to claim 1, further comprising the step of using a fluid heated to a pre-selected temperature for heating the non-target tissue structures in the first treatment mode and using the fluid cooled to a pre-selected temperature for cooling the non-target tissue strutures in the second treatment mode.

7. The method according to claim 1, wherein the radiative energy comprises microwave energy.

8. The method according to claim 1, further comprising the step of using a different (higher or lower) frequency energy (RF, microwave, light or ultrasound) in the first treatment mode than the frequency used in the second treatment mode.

9. The method according to claim 1, further comprising the step of increasing the energy in the second treatment mode.

10. The method according to claim 1, wherein the radiative energy comprises laser energy.

11. The method according to claim 1, wherein the radiative energy comprises ultrasound energy.

12. The method according to claim 11, further comprising the step of focusing the ultrasound energy to direct the ultrasound energy substantially only to the target tissue.

* * * * *